(12) United States Patent
Pawlow

(10) Patent No.: US 9,526,805 B2
(45) Date of Patent: Dec. 27, 2016

(54) STERILIZATION SYSTEM FOR A WATER-INTAKE FINGER AND AIR SPACE OF A BOTTLE FOR A WATER DISPENSER

(71) Applicant: Scandinavian Innovation Group Oy, Pomarkku (FI)

(72) Inventor: Andrzej Pawlow, Riga (LV)

(73) Assignee: SCANDINAVIAN INNOVATION GROUP OY, Pomarkku (FI)

( * ) Notice: Subject to any disclaimer, the term of this patent is extended or adjusted under 35 U.S.C. 154(b) by 452 days.

(21) Appl. No.: 14/347,116

(22) PCT Filed: Sep. 26, 2012

(86) PCT No.: PCT/EP2012/068989
§ 371 (c)(1),
(2) Date: Mar. 25, 2014

(87) PCT Pub. No.: WO2013/045508
PCT Pub. Date: Apr. 4, 2013

(65) Prior Publication Data
US 2014/0255257 A1   Sep. 11, 2014

(30) Foreign Application Priority Data
Sep. 28, 2011   (EP) .................................... 11183038

(51) Int. Cl.
*A61L 2/20* (2006.01)
*B67D 3/00* (2006.01)
*C02F 1/78* (2006.01)

(52) U.S. Cl.
CPC ............. *A61L 2/202* (2013.01); *B67D 3/0035* (2013.01); *C02F 1/78* (2013.01); *B67D 2210/00013* (2013.01); *B67D 2210/00023* (2013.01)

(58) Field of Classification Search
CPC ..... A61L 2/202; B67D 3/0032; B67D 3/0035; B67D 2210/00013; B67D 2210/00023; C02F 1/78
See application file for complete search history.

(56) References Cited

U.S. PATENT DOCUMENTS

| 5,328,059 | A | * | 7/1994 | Campbell ............ B67D 7/0288 141/346 |
| 5,366,619 | A | | 11/1994 | Matsui et al. |
| 7,422,684 | B1 | | 9/2008 | Davis et al. |

FOREIGN PATENT DOCUMENTS

WO   WO 2006/015480 A1   2/2006

OTHER PUBLICATIONS

International Search Report of PCT/EP2012/068989, mailed Oct. 29, 2012, 2 pages.

\* cited by examiner

*Primary Examiner* — Timothy Cleveland
(74) *Attorney, Agent, or Firm* — Finnegan, Henderson, Farabow, Garrett & Dunner, L.L.P.

(57) ABSTRACT

A sterilization system uses an ozone-air mixture for treatment of a water-intake finger and an air space of a water source bottle of a water dispenser in which the bottle is installed with its neck downwards for discharge. The system includes a cone for holding the bottle vertically, the water-intake finger for water delivery from the bottle into a reservoir, an ozone generator, and a control device. Two longitudinal channels in the water-intake finger separately deliver water from the bottle into the reservoir and ozone-air mixture delivery into the bottle. The water-intake finger has a preventive cup, to prevent air penetration into the bottle from the air space of the reservoir, having an inlet channel connected to the generator for ozone-air mixture delivery into the preventive cup during water off-take from the (Continued)

reservoir when water poured out of the bottle is replaced with the ozone-air mixture delivered from the generator.

6 Claims, 7 Drawing Sheets

STERILIZATION SYSTEM FOR A WATER-INTAKE FINGER AND AIR SPACE OF A BOTTLE FOR A WATER DISPENSER

This is a U.S. National Phase of PCT/EP2012/068989, filed Sep. 26, 2012, which claims the benefit of priority to EP 11183038.6, filed Sep. 28, 2011, which is incorporated herein by reference.

FIELD OF THE INVENTION

The present invention relates to sterilization systems for water dispensers, and more particularly to sterilization systems for bottle-type water dispensers, and specifically to sterilization systems using ozone. The system can be applied in new water dispensers or used in modernization of existing water dispensers.

PRIOR ART

Sterilizing effects of ozone are widely known and ozone or ozone-air mixture is used in existing sterilization systems of water dispensers. In such systems, an ozone-air mixture from a generator is passed through water in a cold tank and/or is supplied into an air space of the cold tank.

For example, U.S. Pat. No. 6,532,760 describes a dispenser containing a diffuser located in a water reservoir, which is connected to an ozone generator for ozone delivery into water contained in the water reservoir. Here ozone after passing via water is accumulated in an air space of the water reservoir wherefrom some amount of ozone penetrates also into a bottle. However, with such sterilization method the concentration of ozone that has penetrated into the bottle is insufficient for sterilization of air space in the bottle while with increasing amount of ozone carried through water the taste of water is spoiled.

US patent application No. US 2010/0005825 A1 describes a device for ozone sterilization of air in a cold tank of a water dispenser wherein ozone or an ozone-air mixture is delivered not into water contained in the cold tank but into an air space of the cold tank and therefrom is supplied also into a bottle. Here the ozone concentration in the air space of the cold tank and, consequently, in the ozone-air mixture entering into the bottle, may be higher than in the above-mentioned system. However, since the ozone-air mixture enters into the bottle only during water off-take from the dispenser, the amount of ozone entering into the bottle does not prevent the development of microorganisms in the air space of the bottle, especially during long non-use of the water dispenser. Meanwhile, a further increase of the ozone concentration in the air space of the cold tank leads to deterioration of water taste and excessive power consumption for ozone generation.

Thus, in order to ensure the required sterilization of the bottle air space, it is necessary to increase the amount of ozone delivered to the bottle or, which is the same, increase the concentration of ozone in the ozone-air mixture delivered to the bottle.

Likewise, a necessity exists to ensure sterilization of a water-intake finger by directing the flow of a concentrated ozone-air mixture through it, which is especially important when the bottle is removed and the surface of the water-intake finger is contacting the ambient air. One of major problems of bottled water dispensers is their contamination with microorganisms penetrating into the water container of dispenser when the bottle is replaced, since the bottles are often replaced under uncontrolled conditions and in premises that are far from being sterile, such as hospitals, offices and other public places.

Other objectives and advantages of the proposed invention will become clear from the further description.

DISCLOSURE OF THE INVENTION

The above-mentioned objectives, jointly or severally, are reached by providing a sterilization system using an ozone-air mixture for treatment of a water-intake finger and an air space of a water source bottle of a water dispenser in which the bottle is installed with its neck downwards for gravitation discharge of water from the bottle into a water reservoir located inside the dispenser and having an air space comprises:

a cone for holding the bottle with its neck downwards;

the water-intake finger located in a central part of the cone for opening the bottle and water delivery from the bottle into the water reservoir;

an ozone generator producing the ozone-air mixture for sterilization; and a control device for control of the ozone generator, wherein two longitudinal channels are made in the water-intake finger for separate water delivery from the bottle into the water reservoir and ozone-air mixture delivery into the bottle;

the water-intake finger is provided with a preventive cup adapted to prevent from air penetration into the bottle from the air space of the water reservoir, the preventive cup being provided with an inlet channel connected to the ozone generator for ozone-air mixture delivery into the preventive cup during water off-take from the water reservoir when water poured out of the bottle is replaced with the ozone-air mixture delivered from the ozone generator.

With such a system the concentration of ozone in the ozone-air mixture delivered to the air space of the bottle may be much higher than in the air space of the water reservoir. Use of a lower concentration of ozone in the air space of the water reservoir reduces the danger to deteriorate organoleptic properties of water while ensuring the necessary sterilization of this reservoir. Here, the increased concentration of ozone in the ozone-air mixture delivered to the air space of the bottle maintains a sterile environment in both the bottle and the water-intake finger.

The system is preferably provided with a contactless human detection sensor for switching-on the ozone generator when a human being is detected within a predetermined area in front of the water dispenser.

Switching-on the ozone generator in a good time when a human being approaches the dispenser and prior to water off-take allows to ensure that just the first portion of the ozone-air mixture delivered into the bottle will have the required ozone concentration.

Preferably the predetermined area in front of the water dispenser consists of at least two zones, the ozone generator has at least two modes of output, and the control device is configured to switch the modes of output of the ozone generator depending on the zone where the human being is detected.

The availability of several human detection zones and the ozone generator mode control according to the zone where a person is detected allows optimizing the ozone generator operation, increasing output of the ozone generator as a person is approaching the dispenser.

The system is preferably provided with a bottle removal sensor and the ozone generator having a mode of enhanced output, wherein the control device is configured to switch on the ozone generator in the mode of enhanced output for sterilization of internal and external surfaces of the water-intake finger and an external surface of the cone when the bottle is removed from the dispenser.

A short-time delivery of ozone-air mixture after removal of the bottle ensures the sterilization of internal surfaces of the water-intake finger as well as its external surfaces and the area of the cone around the finger, thus considerably reducing the risk of microorganisms getting into the dispenser through the finger. Meanwhile, a small excessive pressure inside the water reservoir of the dispenser prevents the external air and microorganisms contained therein from getting inside the dispenser.

Preferably, as a bottle removal sensor, the contactless human detection sensor adjusted to response when a person is within the immediate vicinity of the water dispenser may be used.

The switching-on of the ozone generator in a good time when a person approaches the dispenser and prior to removal of the bottle allows to ensure that just the first portion of the ozone-air mixture getting into the cone and on external surfaces of the water-intake finger will be most concentrated while a small excessive pressure inside the water reservoir of the dispenser prevents the external air and microorganisms contained therein from getting inside the dispenser during replacement of the bottle.

The system may be preferably provided with a water level sensor for a short-time switching-on the ozone generator in the mode of enhanced output for sterilization of internal and external surfaces of the finger and external surface of the cone when the bottle is removed and water level in the reservoir is below a certain level.

In the context of the present application, the sterilization is understood as a reduction in the development level of microbiological environment.

Other advantages of the proposed system will become clear from the further detailed description of exemplary embodiments.

DETAILED DESCRIPTION OF THE INVENTION

The proposed sterilization system for a bottle-type water dispenser ensures the sterilization of external surfaces of a water-intake finger and an air space of a bottle when the bottle is installed, and the sterilization of external and internal surfaces of the water-intake finger and of external surface of a bottle-holder cone when the bottle is removed. The system as well prevents from external air penetration inside the dispenser. An increased pressure of the ozone-air mixture inside the dispenser always forms an "ozone-air curtain" preventing the external air from getting inside the dispenser.

Figure 1:
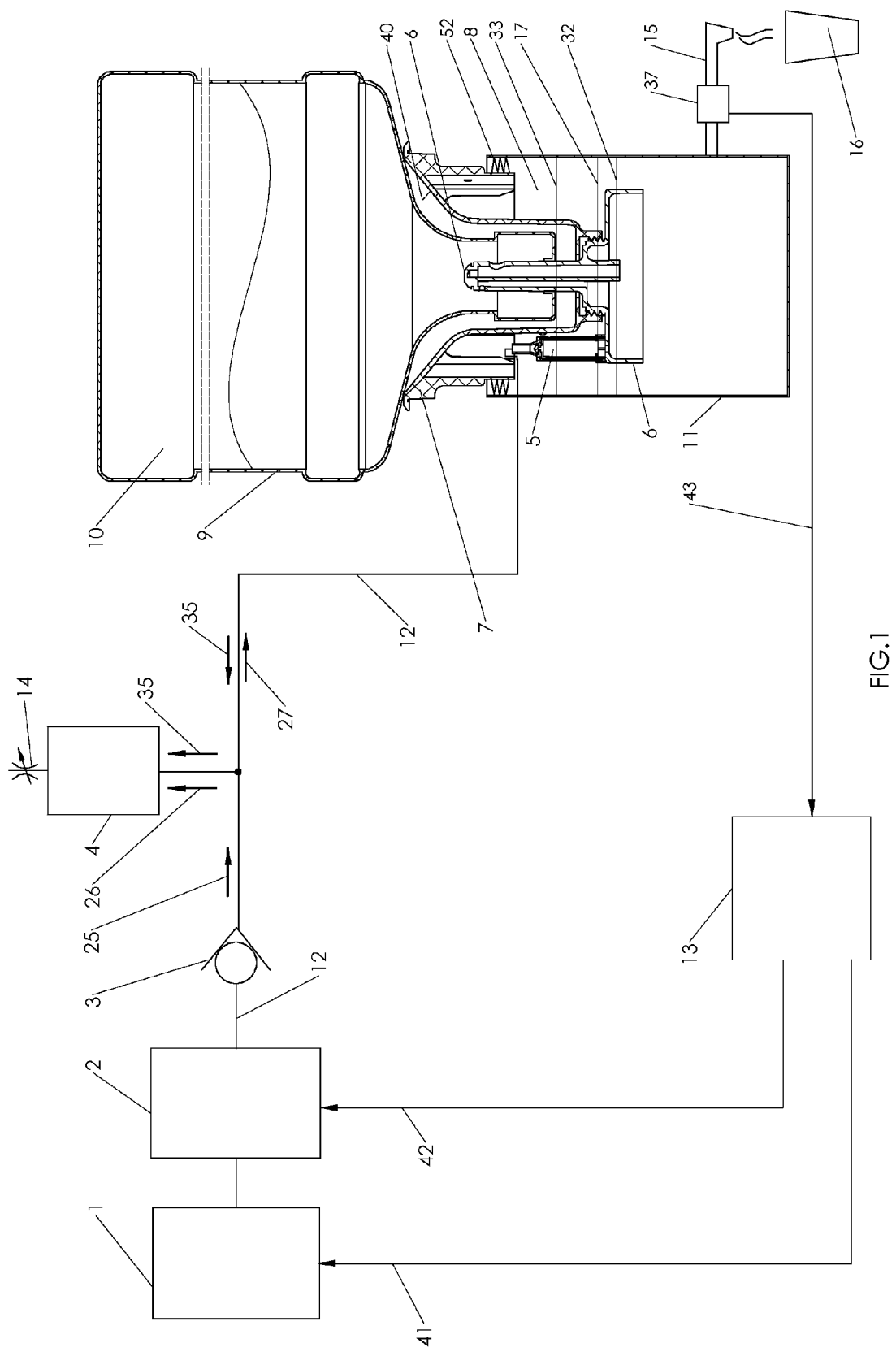
FIG. 1 is a general diagram of an example embodiment of the proposed system.

As shown in FIG. 1, the system of sterilization for a water dispenser consists of:

a bottle 9 with potable water designed to store a stock of potable water;

an ozone generator unit consisting of an air pump 1 designed for the air delivery from the atmosphere into the sterilization system; and an ozone generator 2 designed for ozone generation from the air delivered from the pump 1 and delivery thereof into the water dispenser;

delivery pipelines 12 designed to connect the system elements;

a check valve 3 protecting the ozone generator from water and water vapours;

an ozone destructor 4 designed to destruct ozone when the ozone-air mixture is discharged into atmosphere;

an adjustable throttler 14 for generation and maintenance of an optimal excessive pressure in the system when the air pump 1 is working;

a protective distributing valve 5 designed for delivery of the mixture into the water-intake finger 6 and into the air space 10 of the bottle, and for protection from water leakage in case the bottle 9 is damaged. In this embodiment the distributing valve carries out two functions. It serves to prevent water from getting into the system pipeline when a water level in the water reservoir exceeds a permissible level. The valve also serves to discharge an excessive ozone into the water reservoir;

a water-intake finger 6 designed for water delivery from the bottle 9 into a water reservoir 11 up to a working water level 17 and for delivery of the ozone-air mixture into the bottle air space 10;

a bottle-holder cone 7 designed to hold the bottle 9 in vertical position with its neck downwards and to ensure the sealing tightness of a link cone-water reservoir by means of a sealing ring 52, and having two surfaces: an external surface 40 and an internal surface 53;

a control device 13 designed to control switching-on the air pump 1 and the ozone generator 2;.

a delivery tap 15 designed for off-take of water from the water reservoir 11 into a cup 16.

Figure 2:
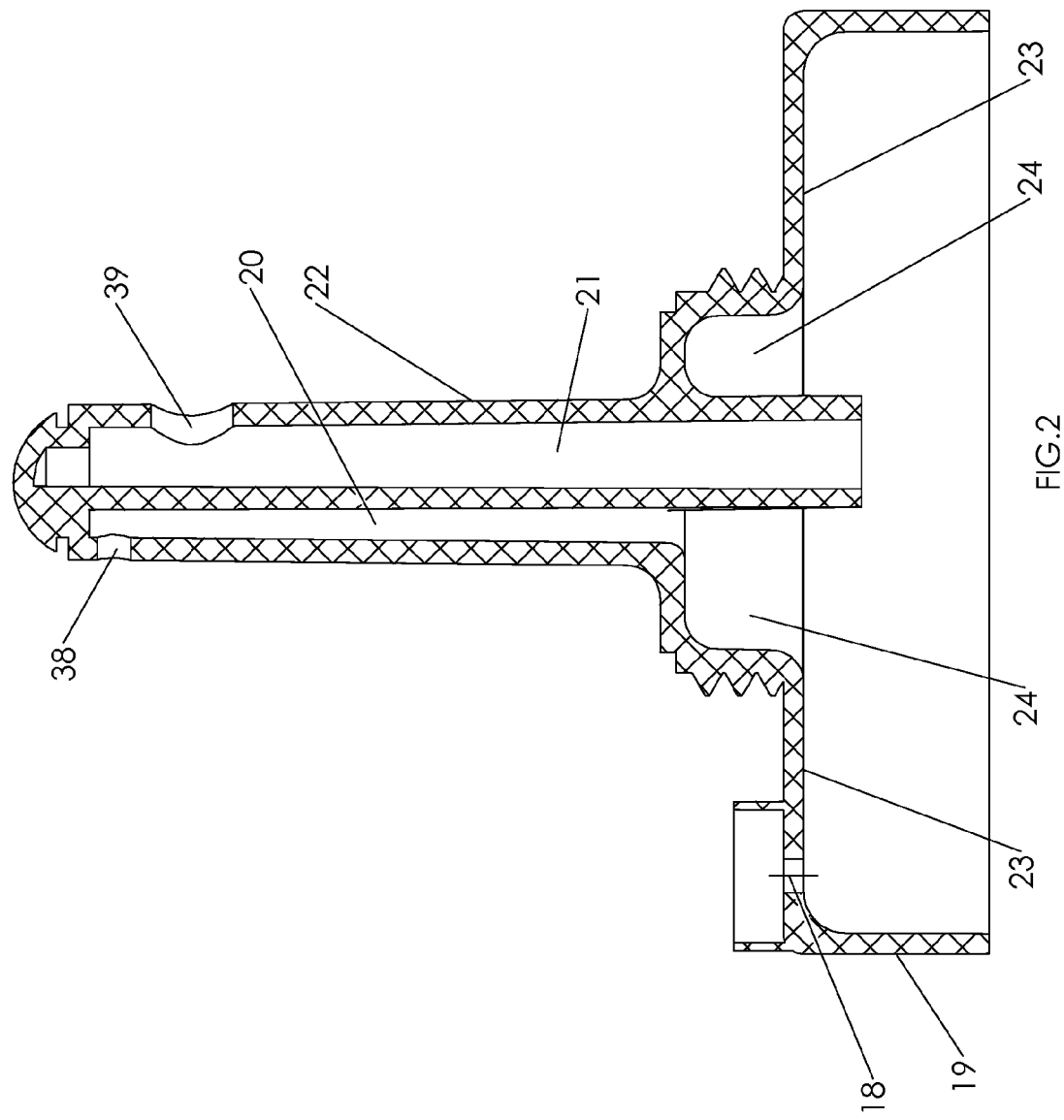
FIG. 2 is an enlarged view of the water-intake finger with a preventive cup.

As shown in FIG. 2, the water-intake finger 6 consists of the following main elements:

a delivery channel 18 to deliver a concentrated ozone-air mixture from an ozone generator into a preventive cup 19 under a slightly excessive pressure due to which a constant ozone concentration is achieved in the ozone-air mixture coming to a bottle air space 10;

a preventive cup 19 designed for prevention of the bottle air space 10 from getting the ozone-air mixture with a low ozone concentration from a water reservoir air space 8 when a water level fluctuates in the water reservoir 11 during water off-take from a delivery tap 15;

a shutoff plane 23, upon reaching of which by water the delivery is stopped of ozone-air mixture into the bottle 9 and water delivery from the bottle 9 is stopped when a working water level 17 is reached in the water reservoir 11;

a technological space 24 located between the inlet into an ozone-air mixture delivery channel 20, by at least 2 mm higher than the shutoff plane 23 and free from obstacles to the ozone-air mixture flow;

a water-intake finger casing 22 designed to open a cork in the bottle 9;

an air delivery channel 20 designed to deliver the ozone-air mixture into the bottle in order to compensate for water that has flown out of the bottle, the channel being separated by a hermetic partition from a water delivery channel 21 and having its length and flow cross-section lesser than the water delivery channel 21, due to which a uniform and continuous water flow from the bottle 9 is reached during water intake into the water reservoir 11;

a bottle water delivery channel 21 for delivery of water from the bottle 9 into the water reservoir 11, the channel outlet being at least 3 mm below the shutoff plane 23 in order to provide the uniformity of the water flow, and at least 15 mm above the end of the preventive cup 19 in order to provide the performance of the preventive cup functions.

A typical single shot water off-take is about 120-180 ml and approximately the same water volume is replaced in the bottle for which purpose nearly the same volume of air or ozone-air mixture should be delivered into the bottle. Guided by these considerations and taking into account the speed of water flowing out of the dispenser, the internal volume of the preventive cup also shall be about 120-180 ml which ensures that just the concentrated ozone-air mixture gets into the bottle and not the air from the water reservoir.

Now we describe the operation of the sterilization system with reference to the basic operational diagram shown in FIG. 1.

Figure 3:
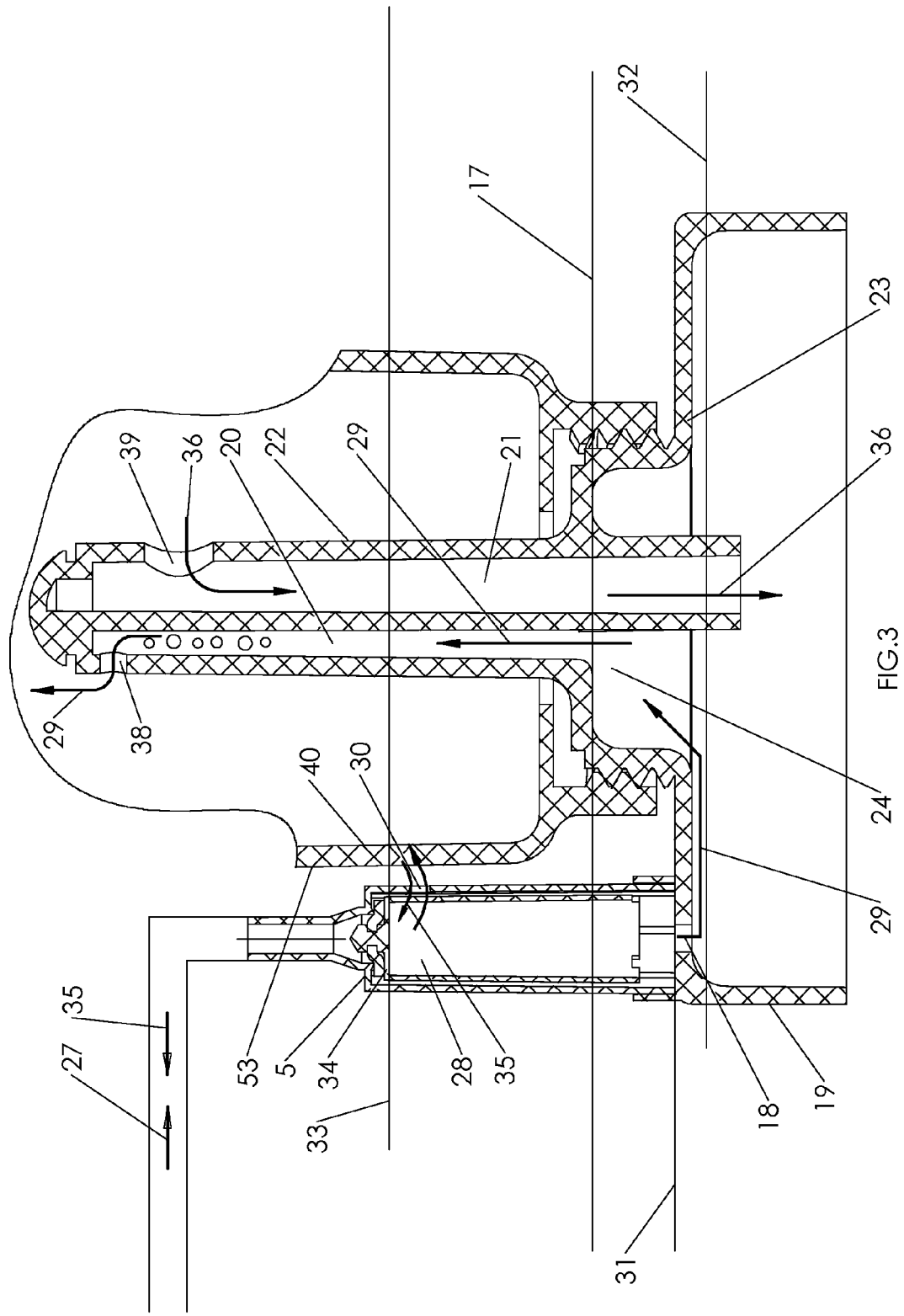
FIG. 3 is an enlarged fragmentary view of the system near a channel for the ozone delivery into the preventive cup.

Upon switching on of the air pump 1 and the ozone generator 2 the air flow gets into the ozone generator where it is enriched with ozone thus forming an ozone-air mixture that is fed through the delivery pipelines 12 into the check valve 3 which prevents the formation of a return flow of the ozone-air mixture and further the ozone-air mixture flow 25 is divided into two flows: the ozone-air mixture flow 26 into the destructor and the ozone-air mixture flow 27 into the protective distributing valve 5. The first flow 26 is directed into the destructor 4 and after the destruction of ozone it is discharged into atmosphere via the adjustable throttler 14 while the second flow 27 is led through the delivery pipeline 12 into the protective distributing valve 5 located inside the water reservoir 11 and connected with its outlet with the channel 18 of ozone-air mixture delivery into the preventive cup 19. For further consideration of operation principles of the system refer to FIG. 3 and examine situation when water in the water reservoir is on the working level 17, water off-take through the delivery tap 15 does not take place, a locking float 34 of the protective distributing valve 5 is in its open position and does not hamper the ozone-air mixture flow. In this situation the flow 28 of the ozone-air mixture through an outlet opening 30 of the distributing valve 5 comes into a water reservoir air space 8 and produces an excessive pressure of the ozone-air mixture in this space which is set by the adjustable throttler 14 or, if such is not available, by the resistance to the flow of the destructor 4. The channel 18 of the ozone-air mixture delivery into the preventive cup 19 is covered by water, the ozone-air mixture does not get into the bottle air space 10, water from the bottle 9 is held by a negative pressure in a bottle air space 8 and does not come into the water reservoir 11. Upon water off-take from the delivery tap 15 the water level in the water reservoir 11 is lowering and upon reaching the water level 32 in the water reservoir allowing the delivery of ozone-air mixture into the water bottle, the ozone-air mixture flow 27 is divided into two flows: the flow 28 and the flow 29 directed via the space 24 and the delivery channel 20 into the bottle air space 10, due to the flow 29 the pressure grows in the bottle air space 10 and a water flow 36 develops from the bottle 9 into the water reservoir 11 for compensation of the water taken from the delivery tap 15 and for restoration of the working water level 17 in the water reservoir 11. Upon completion of water off-take from the delivery tap 15 the water level in the water reservoir rises and upon reaching the level 31 the ozone-air mixture delivery into the space 24 stops while the water flow 36 from the bottle 9 into the water reservoir 11 continues filling the water reservoir 11 and the remains of the ozone-air mixture are pushed out by water from the space 24 into the bottle air space 10, upon reaching the working water level 17 in the water reservoir 11 the water flow 36 is stopped until the next lowering of water level down to the level 30. After switching off of the air pump 1 and the ozone generator 2 a reverse flow 35 of the ozone-air mixture occurs from the water reservoir air space and through the ozone destructor 4 and the adjustable throttler 14 gets into atmosphere due to which a pressure equalization with the atmosphere takes place in the water reservoir air space 8, thus reaching the stabilization of the working water level 17 in the water reservoir. In case of fluctuations in the atmospheric pressure and slight variations of the working water level 17 in the water reservoir, said pressure equalization in the water reservoir air space 8 is carried out via the adjustable throttler 14 and the ozone destructor 4. During replacement of the empty bottle 9 at the level 30 in the water reservoir, the ozone-air mixture freely comes from an opening 38 for outlet of ozone-air mixture from the water-intake finger 6 and accumulates in the bottom portion of the bottle-holder cone 7, thus ensuring the sterilization of external surfaces of the water-intake finger casing 22 and the external surface 40 of the cone 7, which prevents a water contamination during the installation of a newly filled bottle 9.

To control the operation of the air pump 1 and the ozone generator 2, a control device 13 and a water-off-take sensor 37 connected therewith are provided. The control device 13 switches on the air pump 1 and the ozone generator 2 upon receipt of a signal "water off-take" 43 from the water-off-take sensor 37 during the water off-take to create an ozone-air mixture flow compensating for the water poured out from the bottle 9, which is a necessary condition for operation of the sterilization system. A time period between the off-takes should be less than or comparable with the time of decomposition of the ozone-air mixture, which, in turn, strongly depends on a temperature of the mixture and under normal conditions is about 30 minutes. To ensure a normal operation of the system in case of lasting breaks between water off-takes from the delivery tap 15, it is necessary to periodically switch on the air pump 1 and the ozone generator 2 with a period not less than 30 minutes in order to maintain the required ozone concentration in the air space of the water reservoir 11.

Figure 4:
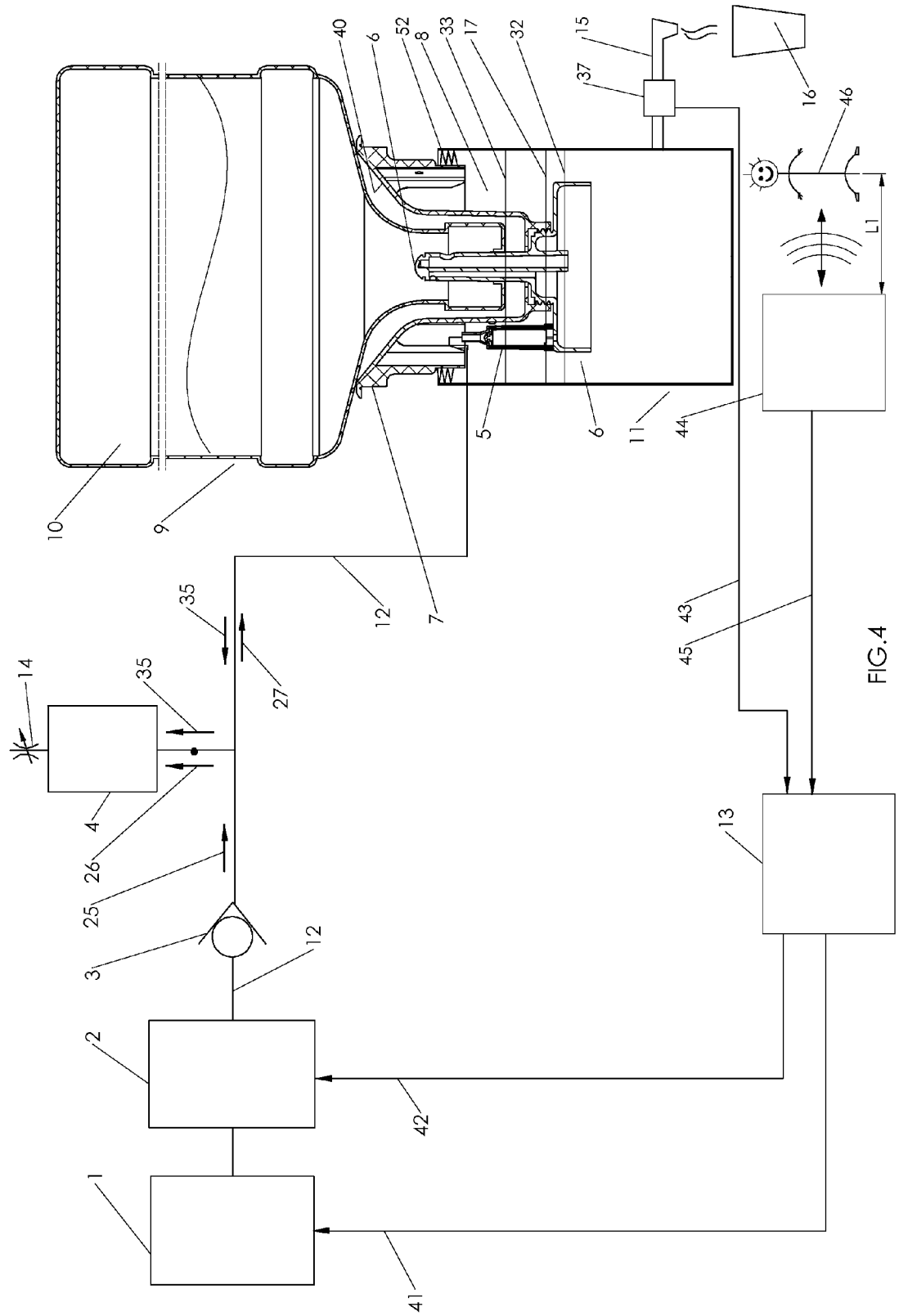
FIG. 4 is a diagram of another embodiment.

FIG. 4 shows an embodiment of the sterilization system differing from the above described in that in this system, for the control of switching on the air pump 1 and the ozone generator 2, a contactless human detection sensor 44 is additionally included. The contactless human detection sensor 44 is a device allowing to detect a human presence without a direct contact of a person with the housing of the water dispenser. The contactless human detection sensor 44 forms a signal 45 of human presence in front of the apparatus within distance 0 to 700 mm, this distance being a zone entering which a person as a rule will use the water dispenser (this was confirmed by the experience of practical application of water dispensers) and therefore being usable for preparation of the water dispenser for operation. By signal 45 of human presence in front of the dispenser the control device 13 switches on the air pump 1 and the ozone generator 2 and switches off these devices in case of human absence within the detection area. The application of this contactless human detection sensor 44 allows most efficiently using the sterilization system resource, and in particular, performing more complete treatment of external surfaces of the water-intake finger casing 22 and of external surface 40 of the cone 7.

Figure 5:
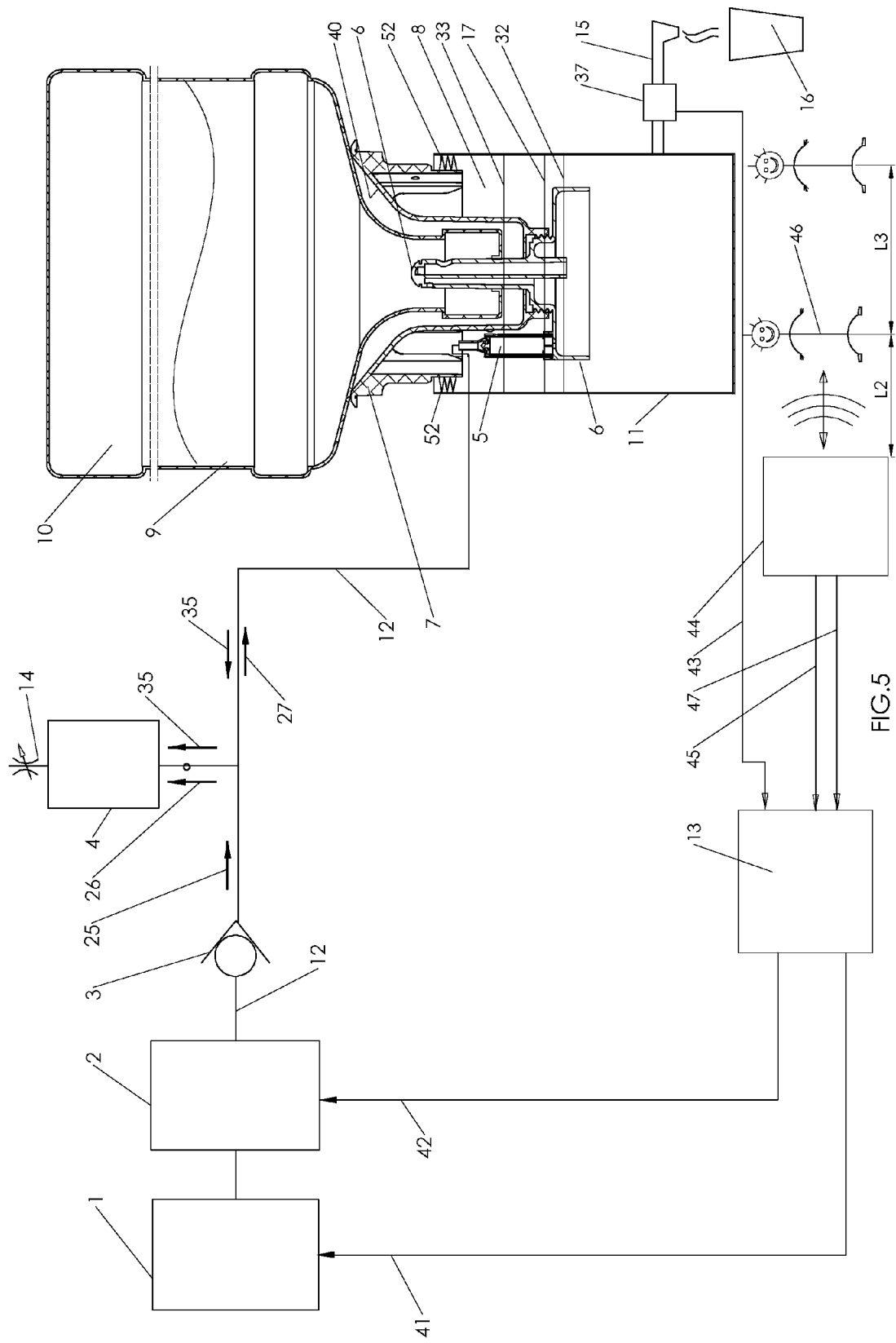
FIG. 5 is a diagram of yet another embodiment.

A basic operational diagram of another embodiment of the invention is presented in FIG. 5. This system differs from that described above in that in this system, for the control of switching on the air pump 1 and the ozone generator 2, a contactless human detection sensor 44 is additionally included with the possibility to detect a person at least in two different zones in front of the water dispenser. The contactless human detection sensor 44 forms a signal 45 of human presence in front of the apparatus within a distance L3 from 250 to 700 mm, this distance being a zone entering which a person as a rule will use the water dispenser (this was confirmed by the experience of practical application of water dispensers) and therefore being usable for preparation of water dispenser for operation. By the signal 45 of human presence in front of the water dispenser the control device 13 switches on the air pump 1 and the ozone generator 2 in a mode of normal working output and switches off these devices in case of human absence within the detection area. The contactless human detection sensor 44 forms a "bottle replacement" signal 47 upon human presence in front of the apparatus within a distance L2 from 0 to 250 mm, this distance defining a zone entering which a person as a rule will carry out the replacement of the empty bottle 9 with a full one. The use of the water dispenser for taking water at such a distance is inconvenient (this was confirmed by the experience of practical application of water dispensers), therefore this distance can be used for switching on the air pump 1 and the ozone generator 2 in the mode of enhanced output for a deeper processing of external surfaces of the water-intake finger casing 22 and of the external surface 40 of the cone 7.

Figure 6:
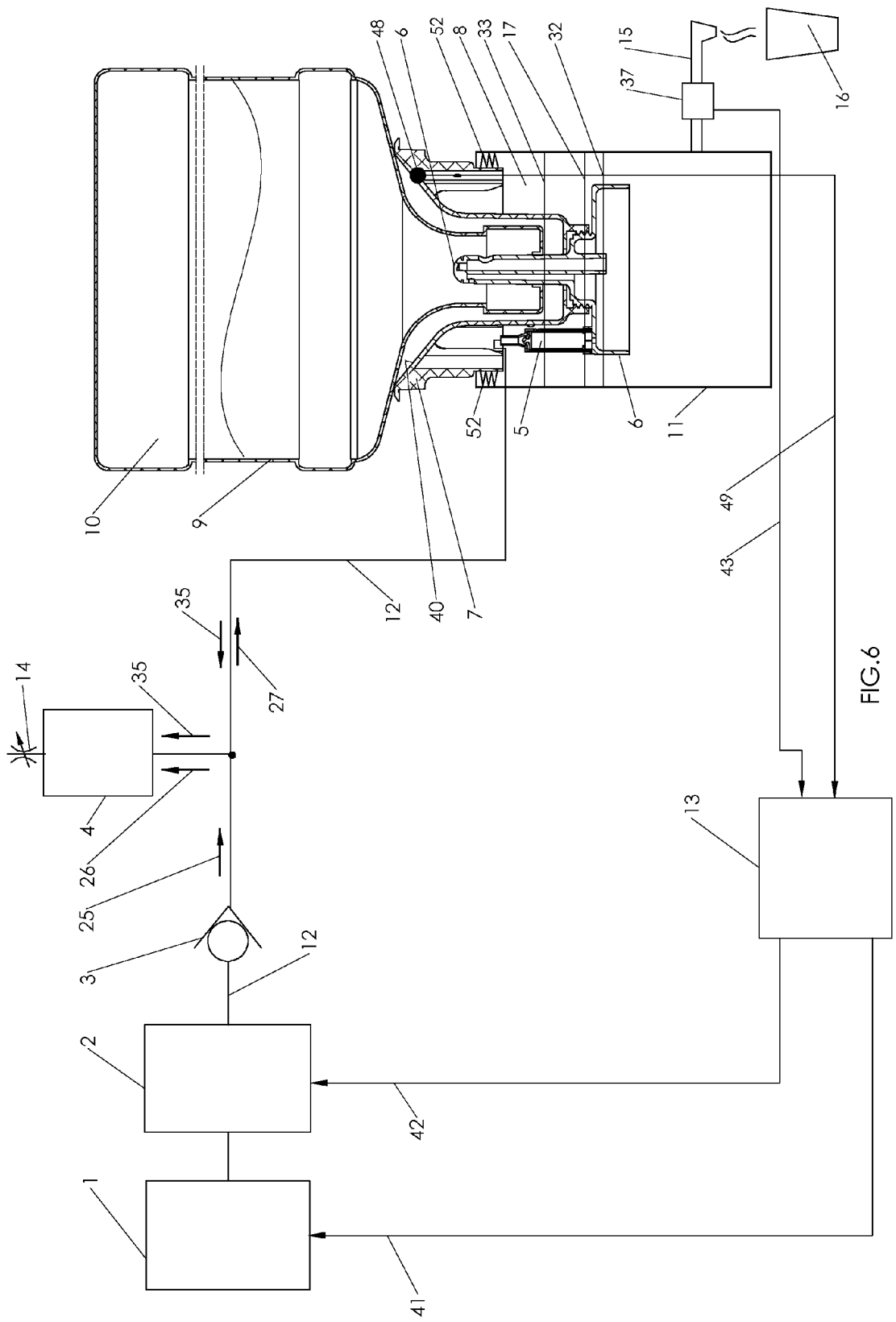
FIG. 6 is a diagram of still another embodiment.

A basic operational diagram of yet another embodiment of the system is shown in FIG. 6. This system for sterilization of water dispenser differs from that described above in that in this system, for the additional control of switching on the air pump 1 and the ozone generator 2, a sensor 48 is additionally included for detection of a bottle installed on the water dispenser. The sensor 48 for detection of a bottle on the water dispenser is a device allowing to detect whether a bottle is installed on the water dispenser and may be either of a contact type or contactless. The sensor 48 for detection of a bottle on the water dispenser forms a "no bottle" signal 49 when there is no bottle on the water dispenser, by which signal the control device 13 switches on the air pump 1 and the ozone generator 2 in the mode of enhanced output for a deeper processing of external surfaces of the water-intake finger casing 22 and of the external surface 40 of the cone 7. Generation of a certain excessive pressure in the preventive cup 19 and in the water-intake finger 6 when the bottle is removed always ensures the formation of an "ozone-air curtain" preventing the external air and microorganisms contained therein from getting into the water dispenser through channels in the water-intake finger 6.

Referring back to FIG. 4 we describe another embodiment of the invention. In this embodiment, the system differs from that described above in that in this system, for the additional control of switching on the air pump 1 and the ozone generator 2, a contactless human detection sensor 44 is included instead of the sensor 48 for detection of a bottle on the water dispenser. The contactless human detection sensor 44 forms a "bottle replacement" signal 47 upon human presence in front of the dispenser within a distance L1 from 0 to 250 mm, this distance representing a zone entering which a person as a rule will carry out the replacement of the empty bottle 9 with a full one while the use of the water dispenser for taking water at such a distance is inconvenient (this was confirmed by the experience of practical application of water dispensers), and therefore this distance can be used for switching on the air pump 1 and the ozone generator 2 in the mode of enhanced output for a deeper processing of external surfaces of the water-intake finger casing 22 and of the external surface 40 of the cone 7. Generation of a certain excessive pressure in the preventive cup 19 yet prior to replacement of the bottle always ensures the formation of an "ozone-air curtain" preventing the external air and microorganisms contained therein from getting into the water dispenser through the channels in the water-intake finger 6. This also ensures that already the first portion of the ozone-air mixture will have a required concentration.

Figure 7:
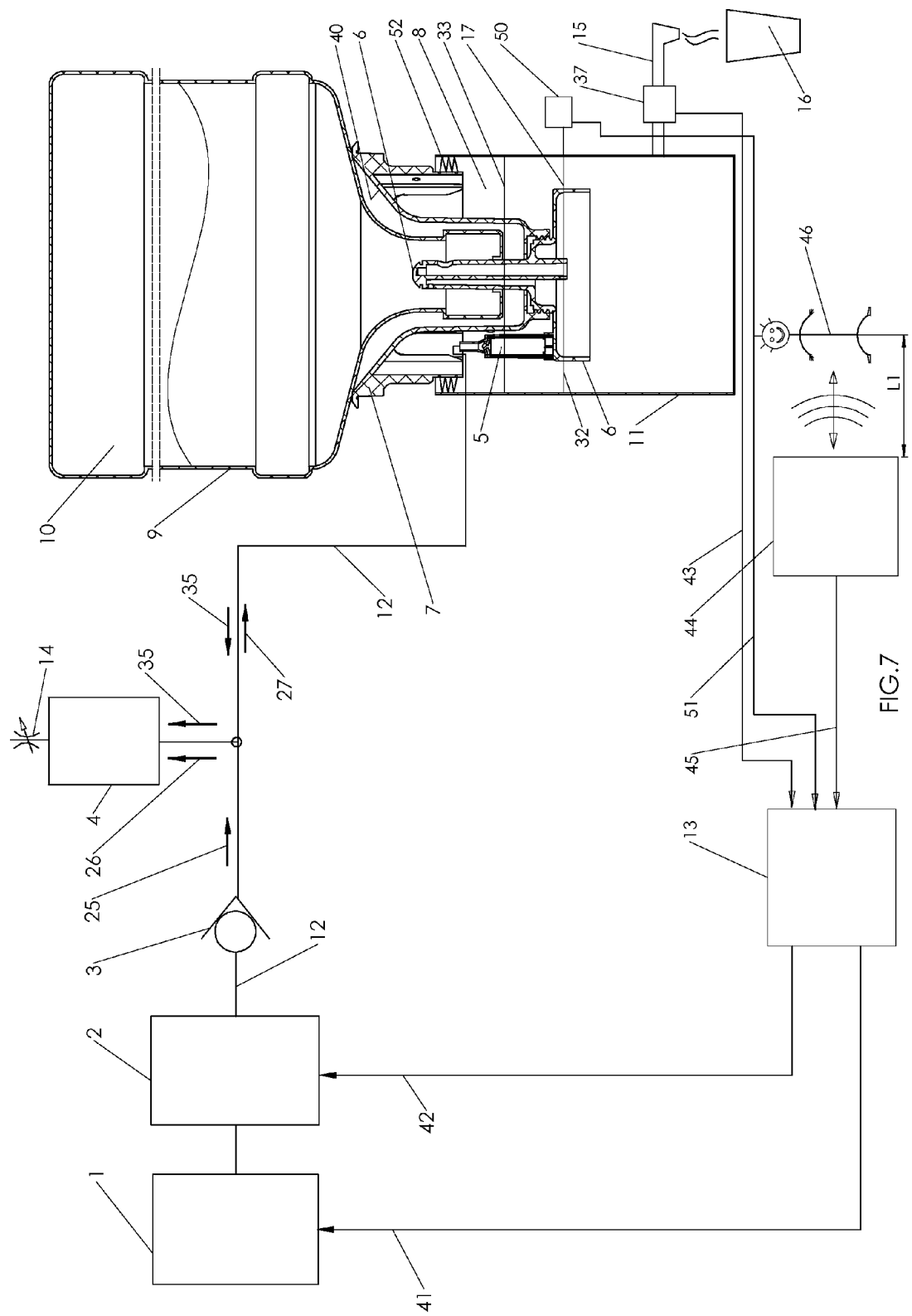
FIG. 7 is a diagram of a further embodiment.

A basic operational diagram of the last embodiment of the invention is shown in FIG. 7. This system differs from that described above in that in this system, for the additional control of switching on the air pump 1 and the ozone generator 2 in the mode of enhanced output, a sensor 50 of water level in the water reservoir is included which forms a "replace bottle" signal 51 as soon as the water level in the reservoir has lowered below the water level 32 in the water reservoir allowing the delivery of the ozone-air mixture into the water bottle as an additional factor for the "replace bottle" signal 47 because the bottle replacement can take place also before there is no more water in the bottle 9 upon human presence in front of the apparatus within a distance L1 from 0 to 250 mm.

Thus, the proposed sterilization system has the following advantages:

the system provides a reliable sterilization of an air space in the water source bottle by ozone-air mixture while preserving water taste;

the system provides sterilization of the water-intake finger and the area of the cone around the finger;

the proposed system also provides an excessive pressure of the ozone-air mixture in the water-intake finger upon removal/replacement of a bottle thus creating an effective ozone-air mixture curtain that is always preventing the external air from getting into the dispenser.

LIST OF POSITIONS IN THE DRAWINGS

No. Description
1 Air pump
2 Ozone generator
3 Check valve
4 Ozone destructor
5 Protective distributing valve
6 Water-intake finger
7 Cone for holding the bottle in vertical position
8 Air space of water reservoir
9 Bottle
10 Air space of bottle
11 Water reservoir
12 Delivery pipelines
13 Control device
14 Adjustable throttler 15 Delivery tap
16 Cup
17 Working water level in the water reservoir
18 Channel for delivery of ozone-air mixture into preventive cup
19 Preventive cup
20 Air delivery channel
21 Water delivery channel
22 Water-intake finger casing
23 Shutoff plane
24 Technological space
25 Ozone-air mixture flow after ozone generator
26 Ozone-air mixture flow after ozone generator into ozone destructor
27 Ozone-air mixture flow after ozone generator into distributing valve
28 Ozone-air mixture flow after distributing valve into air space of water reservoir
29 Ozone-air mixture flow after distributing valve into air space of water bottle
30 Outlet opening of distributing valve
31 Water level in the water reservoir locking ozone-air mixture delivery into air space of water bottle
32 Water level in the water reservoir allowing ozone-air mixture delivery into air space of water bottle
33 Water level in the water reservoir for locking of distributing valve
34 Locking float of distributing valve
35 Ozone-air mixture flow from air space of the water reservoir
36 Water flow from bottle into the water reservoir
37 Water-off-take sensor
38 Opening for outlet of ozone-air mixture from water-intake finger into bottle
39 Opening for water outlet from bottle into water-intake finger
40 External surface of cone for holding bottle in vertical position
41 Control signal for switching of air pump
42 Control signal for switching of ozone generator
43 Control signal for water-off-take sensor
44 Contactless human detection sensor
45 Signal from human detection sensor—no human
46 Human being
47 Signal from human detection sensor—bottle replacement
48 Sensor of bottle presence on water dispenser
49 Signal from bottle presence sensor—no bottle
50 Water level sensor
51 Signal from water level sensor—replace bottle
52 Sealing ring
53 Internal surface of cone

The invention claimed is:

1. A sterilization system using an ozone-air mixture for treatment of a water-intake finger and an air space of a water source bottle of a water dispenser in which the bottle is installed with its neck downwards for gravitation discharge of water from the bottle into a water reservoir located inside the dispenser and having an air space, the system comprising:
a cone for holding the bottle with its neck downwards;
the water-intake finger located in a central part of the cone for opening the bottle and water delivery from the bottle into the water reservoir;
an ozone generator producing the ozone-air mixture for sterilization; and
a control device for control of the ozone generator, wherein
two longitudinal channels are made in the water-intake finger for separate water delivery from the bottle into the water reservoir and ozone-air mixture delivery into the bottle; and wherein
the water-intake finger is provided with a preventive cup adapted to prevent air penetration into the bottle from the air space of the water reservoir, the preventive cup being provided with an inlet channel connected to the ozone generator for ozone-air mixture delivery into the preventive cup during water off-take from the water reservoir when water poured out of the bottle is replaced with the ozone-air mixture delivered from the ozone generator.

2. The system of claim 1 provided with a contactless human detection sensor for switching-on the ozone generator when a human being is detected within a predetermined area in front of the water dispenser.

3. The system of claim 2 wherein the predetermined area in front of the water dispenser consists of at least two zones, the ozone generator has at least two modes of output, and the control device is configured to switch the modes of output of the ozone generator depending on a zone where the human being is detected.

4. The system of claim 1 provided with a bottle removal sensor and the ozone generator having a mode of enhanced output, wherein the control device is configured to switch on the ozone generator in the mode of enhanced output for sterilization of internal and external surfaces of the water-intake finger and an external surface of the cone when the bottle is removed.

5. The system of claim 4 wherein the bottle removal sensor is a contactless human detection sensor adjusted for response when a human being is located within an immediate vicinity of the water dispenser.

6. The system of claim 5 provided with a water level sensor for switching-on the ozone generator in the mode of the enhanced output for sterilization of internal and external surfaces of the water-intake finger and of an external surface of the cone when the bottle is removed and water level in the water reservoir is below a certain level.

\* \* \* \* \*